(12) United States Patent
Stenzel et al.

(10) Patent No.: US 7,691,138 B2
(45) Date of Patent: *Apr. 6, 2010

(54) METHOD AND DEVICE FOR PROVIDING FULL PROTECTION TO A STENT

(75) Inventors: Eric B. Stenzel, Galway (IE); Ronald A. Sahatjian, Lexington, MD (US); Sheng-ping Zhong, Northborough, MD (US); Kinh-Luan D. Dao, Randolph, MD (US); Peter L. Dayton, Brookline, MD (US); Daniel J. Kalashian, Marlborough, MD (US); Stephen Griffin, Sunnyvale, CA (US); Thomas Yung-hui Chien, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 412 days.

This patent is subject to a terminal disclaimer.

(21) Appl. No.: 11/011,233

(22) Filed: Dec. 14, 2004

(65) Prior Publication Data

US 2005/0096724 A1 May 5, 2005

Related U.S. Application Data

(63) Continuation of application No. 10/142,008, filed on May 8, 2002, now Pat. No. 6,830,575.

(51) Int. Cl.
*A61F 2/06* (2006.01)
(52) U.S. Cl. ...................... 623/1.11; 606/108
(58) Field of Classification Search ................ 623/1.11, 623/1.12, 1.15, 1.16; 606/108, 194, 195, 606/198
See application file for complete search history.

(56) References Cited

U.S. PATENT DOCUMENTS 4,950,227 A * 8/1990 Savin et al. ................. 623/1.12

(Continued)

FOREIGN PATENT DOCUMENTS

EP 1 034 752 A1 9/2000

(Continued)

OTHER PUBLICATIONS

U.S. Appl. No. 10/142,008, filed May 8, 2002, 6,830,575 B2, Stenzel et al.

*Primary Examiner*—Pedro Philogene
(74) *Attorney, Agent, or Firm*—Vidas, Arrett & Steinkraus P.A.

(57) ABSTRACT

A catheter comprises a catheter shaft, at least a portion of which defines a medical device receiving region, and at least one sleeve. The at least one sleeve comprises a tubular member constructed and arranged to transition between an extended state and a retracted state. The tubular member has a first portion being engaged to a portion of the catheter shaft adjacent to the medical device receiving region. In the extended state a second portion is constructed and arranged to at least partially overlay the medical device receiving region. In the retraced state the second portion is removed from about the medical device receiving region. At least one of the first portion and the second portion of the tubular member are at least partially constructed from a shape memory material.

20 Claims, 7 Drawing Sheets

U.S. PATENT DOCUMENTS

| | | | |
|---|---|---|---|
| 5,108,416 A | 4/1992 | Ryan et al. | |
| 5,403,341 A * | 4/1995 | Solar | 606/198 |
| 5,549,635 A * | 8/1996 | Solar | 623/1.12 |
| 5,571,135 A | 11/1996 | Fraser et al. | 606/198 |
| 5,628,755 A * | 5/1997 | Heller et al. | 606/108 |
| 5,645,564 A | 7/1997 | Northrup et al. | 606/205 |
| 5,779,732 A * | 7/1998 | Amundson | 623/1.15 |
| 5,980,530 A * | 11/1999 | Willard et al. | 623/1.11 |
| 6,030,407 A | 2/2000 | Eidenschinek | 606/198 |
| 6,063,112 A * | 5/2000 | Sgro | 623/1.12 |
| 6,068,634 A * | 5/2000 | Lorentzen Cornelius et al. | 623/1.11 |
| 6,168,617 B1 | 1/2001 | Blaeser et al. | 623/1.11 |
| 6,206,888 B1 * | 3/2001 | Bicek et al. | 606/108 |
| 6,270,504 B1 * | 8/2001 | Lorentzen Cornelius et al. | 606/108 |
| 6,270,521 B1 | 8/2001 | Fischell et al. | 623/1.11 |
| 6,280,412 B1 | 8/2001 | Pederson, Jr. et al. | 604/103.07 |
| 6,281,262 B1 | 8/2001 | Shikinami | |
| 6,350,278 B1 | 2/2002 | Lenker et al. | 623/1.12 |
| 6,371,979 B1 | 4/2002 | Bayar et al. | 623/1.12 |
| 6,387,118 B1 * | 5/2002 | Hanson | 623/1.11 |
| 6,391,032 B2 | 5/2002 | Blaeser et al. | 606/108 |
| 6,391,050 B1 | 5/2002 | Broome | 623/1.11 |
| 6,395,008 B1 | 5/2002 | Ellis et al. | 606/108 |
| 6,398,802 B1 | 6/2002 | Yee | 623/1.13 |
| 6,416,529 B1 * | 7/2002 | Holman et al. | 606/194 |
| 6,478,814 B2 * | 11/2002 | Wang et al. | 623/1.12 |
| 6,554,841 B1 * | 4/2003 | Yang | 606/108 |
| 6,565,595 B1 * | 5/2003 | DiCaprio et al. | 623/1.11 |
| 6,830,575 B2 * | 12/2004 | Stenzel et al. | 606/108 |
| 2001/0012944 A1 | 8/2001 | Bicek | 606/108 |
| 2001/0012959 A1 | 8/2001 | Blaeser et al. | 623/1.11 |
| 2001/0029352 A1 | 10/2001 | Gandhi et al. | |
| 2001/0029378 A1 | 10/2001 | Blaeser et al. | 606/108 |
| 2001/0032008 A1 | 10/2001 | Wang et al. | |
| 2002/0029046 A1 | 3/2002 | Cornelius et al. | 606/108 |
| 2002/0072789 A1 * | 6/2002 | Hackett et al. | 623/1.12 |

FOREIGN PATENT DOCUMENTS

| | | |
|---|---|---|
| JP | 3-42459 | 11/1992 |
| WO | 96/31249 | 10/1996 |
| WO | WO 00/59404 | 10/2000 |
| WO | 01/58366 A1 | 8/2001 |
| WO | 02/22051 | 3/2002 |

* cited by examiner

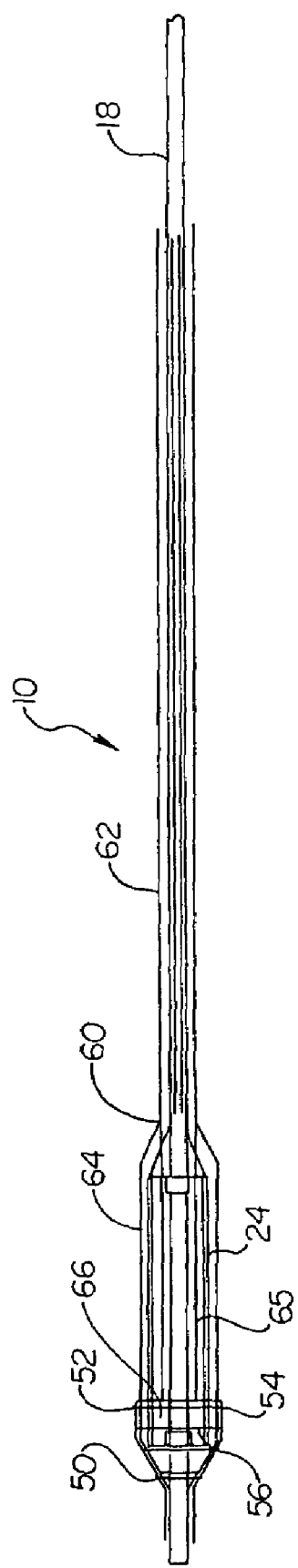
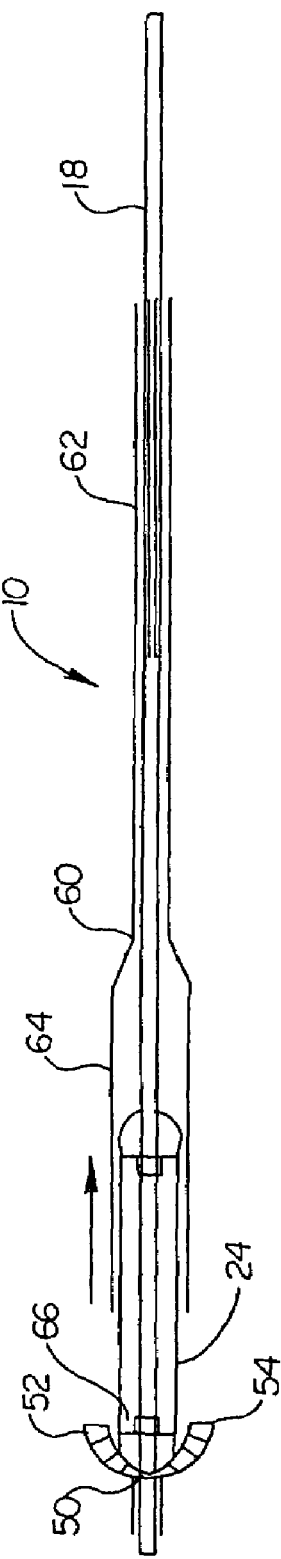

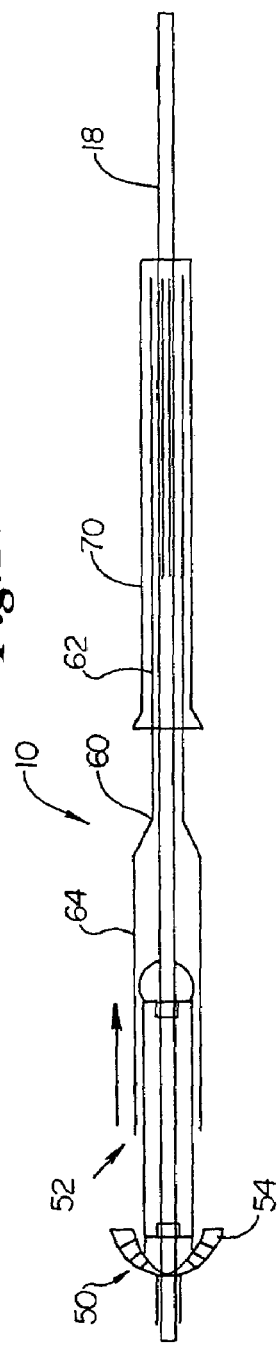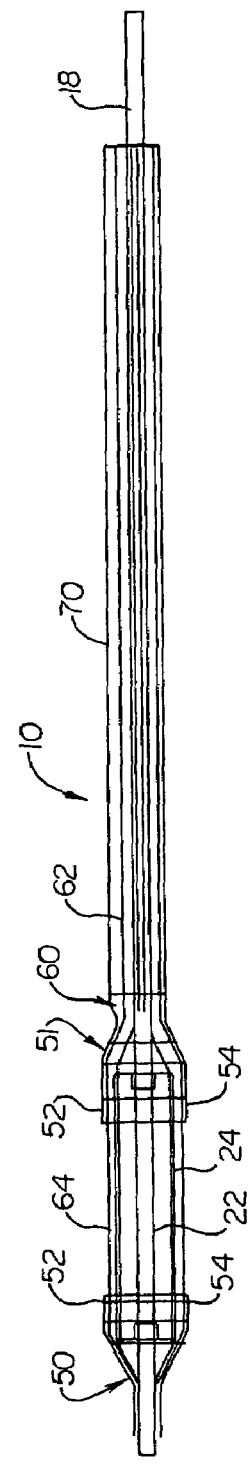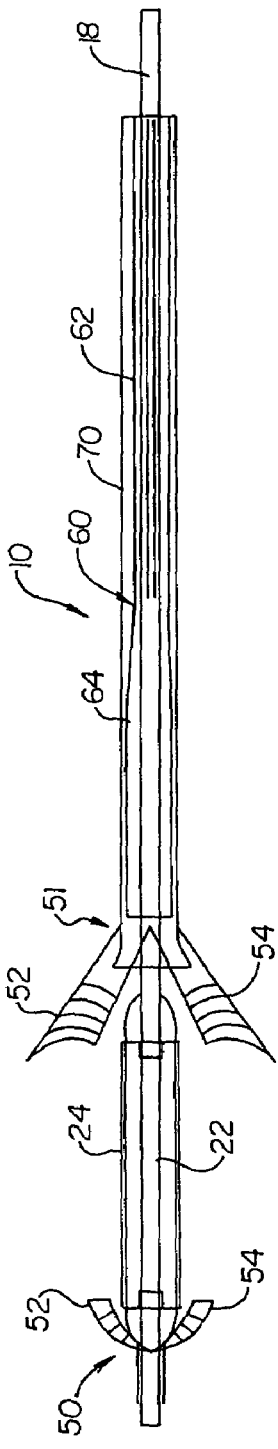

METHOD AND DEVICE FOR PROVIDING FULL PROTECTION TO A STENT

CROSS-REFERENCE TO RELATED APPLICATIONS

This application is a Continuation application from application Ser. No. 10/142,008, filed May 8, 2002, the contents of which is hereby incorporated by reference.

Not Applicable

STATEMENT REGARDING FEDERALLY SPONSORED RESEARCH

Not Applicable

BACKGROUND OF THE INVENTION

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent can support and/or reinforce the vessel walls while maintaining the vessel in an open, unobstructed condition.

Stents may be used in a wide variety of locations in the body including in coronary arteries, renal arteries, peripheral arteries including iliac arteries, arteries of the neck and cerebral arteries. Stents are also used in other bodily locations including but not limited to arteries, veins, biliary ducts, urethras, fallopian tubes, bronchial tubes, the trachea, the esophagus and the prostate.

Stents typically are self-expanding, balloon expandable or a hybrid of the two. Self-expanding stents may be made of shape memory metals such as nitinol, shape memory polymer materials, or constructed of non-shape memory metals but of a design which exhibits self-expansion characteristics. Balloon expandable stents are typically delivered on a balloon and the balloon is used to expand the stent. Hybrid stents may have both self-expanding properties and balloon expanding properties.

Typically, stents are delivered to desired bodily locations via the use of catheters. A catheter comprising a stent is introduced into a bodily vessel and advanced through the vasculature in the body until the stent is positioned in a desired location. Often, the stent can be protected by a retractable sheath which is disposed about the stent and which increases the profile of the delivery catheter. The sheath may be removed from about the stent via the use of a retraction device such as a pull-wire, pull rod or a catheter tube which is connected to the sheath. As part of the removal, the sheath may optionally be rolled off of the stent. In the case of self-expanding stents, the sheath may also restrain the stent from self-expanding. Once at the desired location, the stent is either allowed to self-expand and/or balloon expanded. In the case of self-expanding stents, the self-expansion may occur as a result of the removal of the sheath from about the stent.

Some stent delivery and deployment assemblies are known which utilize restraining sleeves that overlie one or more portions of the stent prior to delivery. U.S. Pat. No. 4,950,227 to Savin et al, relates to an expandable stent delivery system in which a sleeve overlaps the distal or proximal margin (or both) of the stent during delivery. That patent discloses a stent delivery system in which a catheter carries, on its distal end portion, a stent which is held in place around the catheter prior to and during percutaneous delivery by means of one and preferably two sleeves. The sleeves are positioned around the catheter with one end portion attached thereto and overlap an end portion(s) of the stent to hold it in place on the catheter in a contracted condition. The stent is expandable by means of the expandable balloon on the catheter. During expansion of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Copending U.S. patent application Ser. No. 09/407,836 which was filed on Sep. 28, 1999 and entitled Stent Securement Sleeves and Optional Coatings and Methods of Use, and which is incorporated in its entirety herein by reference, provides for a stent delivery system having sleeves. In U.S. Ser. No. 09/407,836 the sleeves may be made up of a combination of polytetrafluoroethylene (PTFE) as well as one or more thermoplastic elastomers.

In many cases a catheter system employing one or more stent retaining sheath or sleeve will require a pull-back member and an associated pull back mechanism for drawing the sheath or sleeve off of the stent prior to stent delivery. Such pull back members may be bulky and undesirably increase the profile and/or complexity of the catheter system and its use. Many catheter systems employ pull back mechanisms which fold the sheath or sleeve over itself, thus undesirably increasing the profile of the catheter prior to withdrawal of the catheter. In the case of systems employing self-retracting sleeves or socks, the self-retracting sleeves may also be configured to fold over during retraction. Because folding of sheathes, sleeves or socks may be difficult or undesirable in the restrictive confines of a body lumen it would be desirable to provide a stent retaining device which is both self-retracting and which does not rely on a folding principle to retract off of the stent.

The entire content of all of the patents listed within the present patent application are incorporated herein by reference.

Without limiting the scope of the invention a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to several embodiments. In at least one embodiment the invention is directed to a catheter having at least one component that is at least partially constructed from a shape memory material. Preferably, the catheter component at least partially constructed from a shape memory material is a sheath, sleeve and/or sock. The shape memory properties provided to the sheath, sleeve and/or sock allows the sheath, sleeve and/or sock to be retractable from a first position overlying at least a portion of an implantable medical device to a second position off of the implantable medical device without requiring a pull back member and without the need to fold any portion of the sheath, sleeve and/or sock. Other catheter components which may be at least partially constructed from a shape memory material include the catheter shaft, an inflation member or balloon, medical device mounting bodies, and any combinations or portions thereof.

In at least one embodiment of the invention a catheter employs one or more medical device retaining sleeves which include one or more wing portions. The wing portions are constructed and arranged to retain a medical device in a reduced state about the catheter. When the one or more sleeves are activated the wing portions release the medical device thereby allowing it to expand to an expanded state. In an alternative embodiment the wing portions include retaining members that retain the wing portions and the medical device in a reduced state. The retaining members may be constructed from a shape memory material and/or may be frangible or expandable. When the retaining members are triggered to expand or are broken the winged portions release the medical device.

In at least one embodiment of the invention a catheter may be equipped with a retractable sheath or sleeve which may be disposed about an implantable medical device or portion thereof. The retractable sheath may be held onto the medical device by one or more sleeves having wing portions. When the wing portions release the medical device, the retractable sheath is retracted from the medical device as well.

BRIEF DESCRIPTION OF THE SEVERAL VIEWS OF THE DRAWINGS

A detailed description of the invention is hereafter described with specific reference being made to the following drawings.

FIG. 16 is a side elevational view of an embodiment of the invention wherein a catheter comprises a retractable body sheath and a distally mounted winged sleeve.

FIG. 17 is a side elevational view of the embodiment shown in FIG. 16 wherein the winged sleeve is shown in the released state and the body sheath is shown retracting to the retracted state.

FIG. 18 is a side elevational view of an embodiment of the invention similar to that shown in FIG. 16 wherein the catheter further comprises a protective sheath for receiving the retractable body sheath when retracted to the retracted state.

FIG. 19 is a side elevational view of an embodiment of the invention similar to that shown in FIG. 18 wherein the catheter further comprises a proximally mounted winged sleeve.

FIG. 20 is a side elevational view of the embodiment of the invention shown in FIG. 19 wherein the winged sleeves are shown in the released state and the body sheath is shown in the retracted state.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
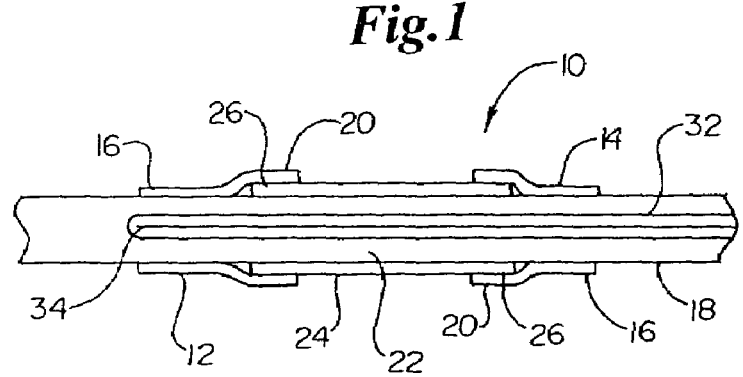
FIG. 1 is a side elevational view of an embodiment of the invention.

In FIG. 1 a first embodiment of the invention is shown wherein a catheter, indicated generally at 10, is equipped with a pair of sleeves 12 and 14. Catheter 10 may be any type of catheter, such as a fixed wire, single operator exchange (SOE)/rapid exchange (RX), over the wire (OTW) or other variety.

In the embodiment shown, a portion 16 of each sleeve 12 and 14 is engaged to the catheter shaft 18. The engaged portion 16 may be engaged to the catheter shaft through the application of an adhesive therebetween; frictional engagement; chemical, heat, or any other form of bonding or welding including laser welding. A second portion 20 of each sleeve 12 and 14 extends over at least a portion of a predetermined area 22 of the catheter shaft 18. In the embodiment shown, predetermined area 22 is configured to removably engage a medical device 24 disposed there about. The medical device 24 is typically a stent, graft, stent-graft, vena cava filter or other implantable medical device hereinafter collectively referred to generally as stents.

In the embodiment shown in FIG. 1 the stent 24 is shown in a reduced state, prior to delivery. The ends 26 of the stent 24 are overlaid by the second portion 20 of the sleeves 12 and 14 respectively. In the case of a self-expanding stent, the sleeves 12 and 14 have sufficient strength to retain the stent 24 in the reduced state and prevent the stent from self-expanding prior to removal of the second portion 20 from the stent ends 26. Where the stent 24 is a hybrid or balloon expandable stent, the sleeves 12 and 14 help to secure the stent 24 into position about a medical balloon 30 such as may be seen in FIG. 3.

The sleeves 12 and 14 are preferably at least partially constructed from at least one shape memory material (SMM) which is preferably a shape memory polymer (SMP). As is well known in the art, devices constructed of SMM may be configured to assume one or two different shapes depending on certain physical parameters which the SMM is exposed to. For example a device constructed from SMM may be configured to transition from a programmed shape to a default shape when the SMM is exposed to a known transition condition, such as a predetermined temperature, pH or other environmental condition.

In the present case suitable SMM materials may range from shape memory metals such as nitinol to SMPs and even natural rubber. In at least one embodiment where the sleeves 12 and 14 are polymeric in nature suitable SMP materials include but are not limited to: thermoplastics such as shape memory polyurethanes, crosslinked trans-polyoctylene rubber, polynorbornene polymers and copolymers and blends thereof with styrene elastomer copolymers, such as Kraton, and polyethylene; styrene butadiene copolymers; PMMA; polyurethane; cross-linked polyethylene; cross-linked polyisoprene; polycycloocetene; bioabsorbable shape memory polymers such as polycaprolactone, copolymers of (oligo) caprolactone, PLLA, PL/D L A copolymers, and/or PLLA PGA copolymers; Azo-dyes and/or Zwitterionic and/or other photo chromatic materials such as those described in "Shape Memory Materials" by Otsuka and Wayman, Cambridge University Press 1998, the entire contents of which being incorporated herein by reference.

Figure 2:
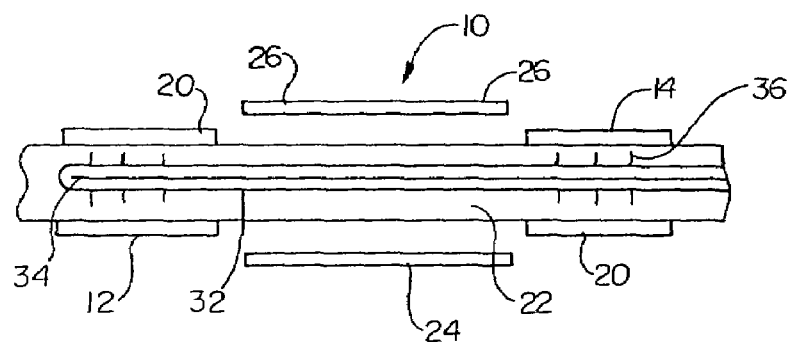
FIG. 2 is a side elevational view of the embodiment of the invention shown in FIG. 1 wherein the sleeves are shown in a retracted position.

In the embodiment shown in FIG. 1 the sleeves 12 and 14 are shown in a programmed shape or length, wherein they respectively overlie the ends 26 of the stent 24. When the sleeves 12 and 14 are exposed to a transition temperature, or other transition condition, the sleeves 12 and 14 will transition to their default length wherein the length of each sleeve is shortened to the extent that the second portions 20 of each sleeve 12 and 14 are longitudinally retracted off of the stent ends 26 such as may be seen in FIG. 2.

While the desirability of a shortening of the sleeves 12 and 14 has been mentioned above, the particular shape of the sleeves 12 and 14 in the programmed state and/or the default state may be widely varied. For example, if desired sleeves 12 and 14 may be provided with a rolling retraction, a lifting or radially directed retraction, or any other change in orientation which results in removing sleeves 12 and 14 from the stent 24.

In order to trigger the transition of the sleeves 12 and 14, the sleeves may be heated to a transition temperature by direct or indirect exposure to a heat source or element 34. Alternatively, the sleeves may be stimulated by mechanical, chemical, optical or other means other than heat to reach a transition state. For example, the element 34 may be an electrically resistive and/or conductive wire, an IR radiation transmitting fiber optic line, or any other transmission medium. Element 34 may also include: a device for the application of ultrasonic energy, a lumen for providing a saline bolus or other substance having a desired temperature or pH. In the embodiments shown, the catheter 10 may include a lumen 32 within which the element 34 may be proximally inserted (or injected in the case of a bolus) into the catheter and advanced to be in proximity to the sleeves 12 and 14. In an embodiment where the stent 24 is a self-expanding stent, the element 34 may also be utilized to trigger the expansion of the stent 24 from the reduced state shown in FIG. 1 to an expanded state shown in FIG. 2. Where the sleeves 12 and 14 are pH sensitive, a saline bolus having a desired pH may be used to trigger transition. In such embodiments however, the lumen 32 will include one or more ports 36 to transmit the bolus to the sleeves 12 and 14 directly.

Figure 3:
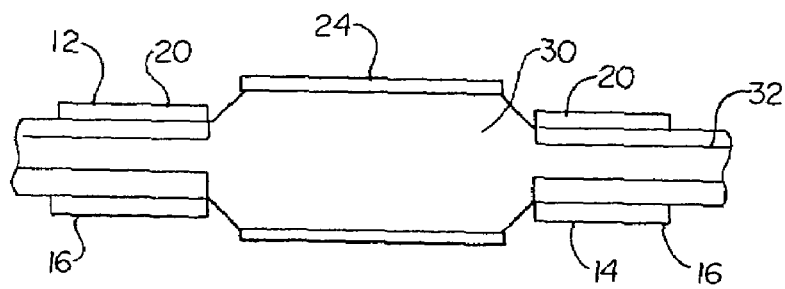
FIG. 3 is a side elevational view of the embodiment of the invention wherein the catheter employs an expansion member to expand the implantable medical device.

In embodiments where the predetermined area 22 includes an inflation balloon 30, such as is shown in FIG. 3. The lumen 32 may also be utilized to inflate the balloon 30. The inflation media (not shown) may be heated to trigger transition of the sleeves 12 and 14 in the manner described.

Figure 4:
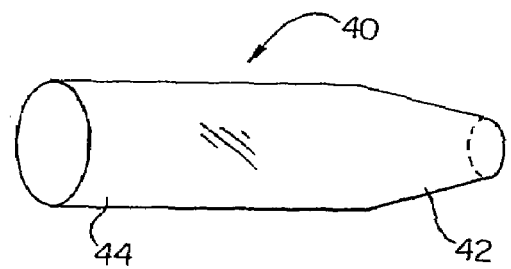
FIG. 4 is a perspective view of an embodiment of the invention.

In an alternative embodiment of the invention shown in FIG. 4, a single SMM sleeve 40 may be configured to retractably overly all or a portion of a medical device mounted on a catheter. In the embodiment shown the sleeve 40 is at least partially constructed from a SMP. The sleeve 40 comprises a first portion 42 which is constructed and arranged to be engaged to a portion of a catheter shaft. A second portion 44 is constructed and arranged to be drawn over a medical device receiving region of the catheter.

Figure 5:
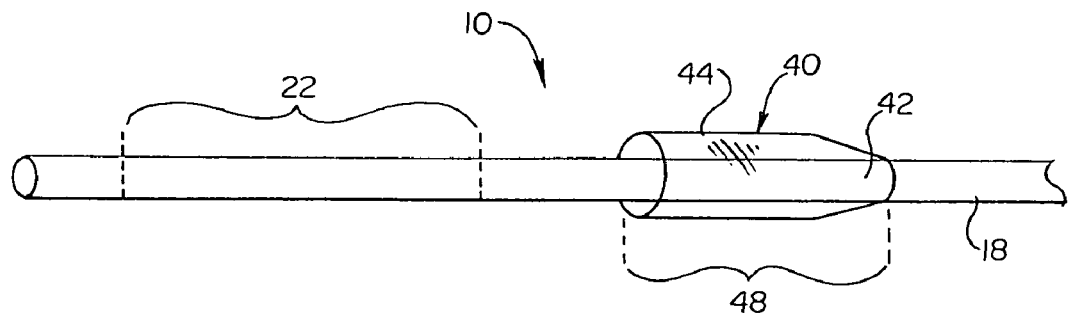
FIG. 5 is a perspective view of the embodiment shown in FIG. 4 wherein the sleeve is shown employed on a catheter shaft but prior to being disposed about an implantable medical device.

As may be seen in FIG. 5, the sleeve 40 may be disposed about a portion of the catheter shaft 18. The first end 42 is adhered, bonded or otherwise engaged to a portion of the shaft 18 adjacent to the medical device receiving region 22. In the embodiment shown the sleeve 40 is mounted proximal to the medical device receiving region 22 in alternative embodiments however, sleeve 40 may be positioned proximal and/or distal of the medical device receiving region 22.

Figure 6:
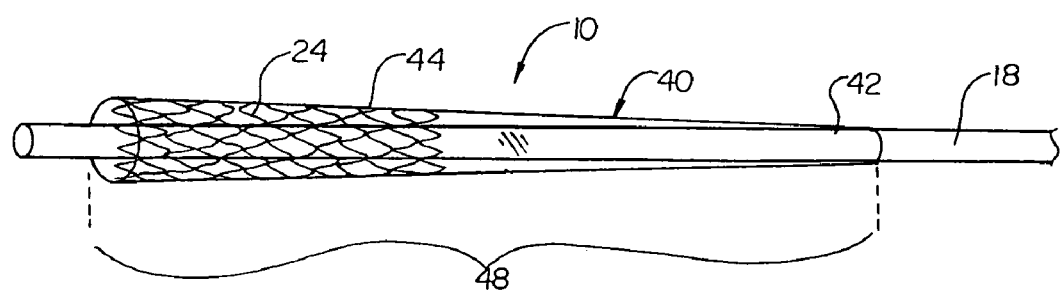
FIG. 6 is a perspective view of the embodiment shown in FIG. 5 wherein the sleeve has been elongated to extend over an implantable medical device.
Figure 7:
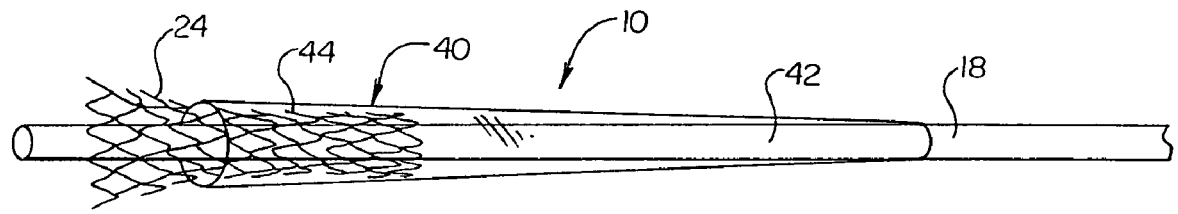
FIG. 7 is a perspective view of the embodiment shown in FIG. 6 wherein the sleeve is shown being retracted from about the medical device.
Figure 8:
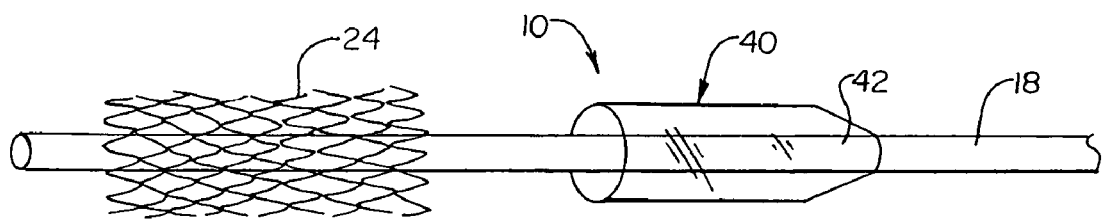
FIG. 8 is a perspective view of the embodiment shown in FIG. 7 wherein the sleeve is shown fully delivered and the implantable medical device is in an expanded state.

When initially placed on the catheter shaft 18, the sleeve 40 is in a default state wherein the length 46 of the sleeve 40 does not extend over any portion of the medical device receiving region 22. Once a stent or other medical device 24 is received by the medical device receiving region 22, the sleeve 40 is elongated to a second length 48 which is the programmed state of the sleeve 40 as is shown in FIG. 6. When the sleeve 40 is in the programmed state, the second portion 44 of the sleeve 40 retainingly engages the stent 24. The sleeve 40 remains in the programmed state until triggered by a transition condition which causes the sleeve 40 to retract back to the original or default state, thereby exposing the stent 24 for delivery, such as is shown in FIGS. 7 and 8.

Figure 9:
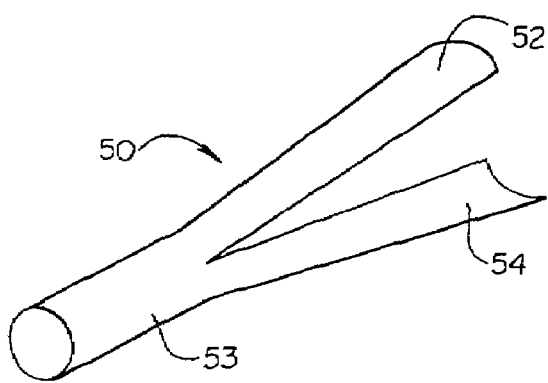
FIG. 9 is a perspective view of an embodiment of the invention.
Figure 10:
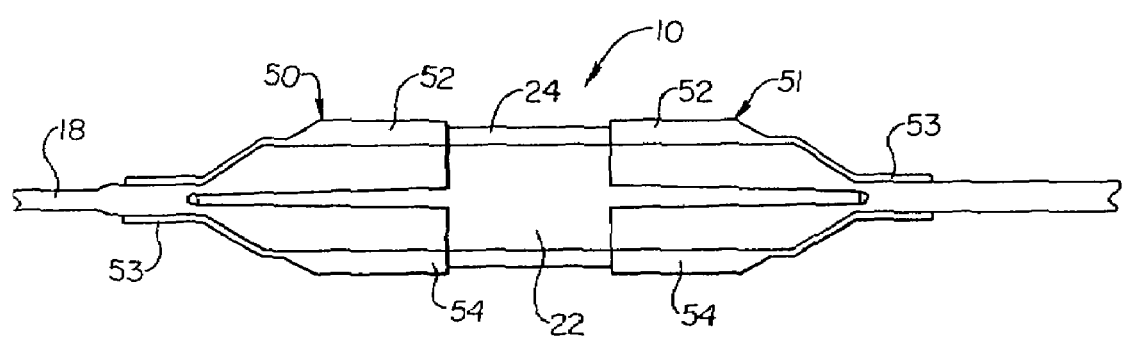
FIG. 10 is a side elevational view of an embodiment of the invention wherein winged sleeves are shown disposed about the ends of an implantable medical device on a catheter.

In yet another embodiment of the invention, a sleeve or sleeves 50, such as is shown in FIG. 9, may include two or more wing members 52 and 54. The wing members 52 and 54 are preferably constructed from a SMP material, which allows the wings to move from a retaining position such as is shown in FIG. 10 to a released position, such as may be seen in FIG. 13 when a transition condition, such as have been previously described, occurs.

Figure 13:
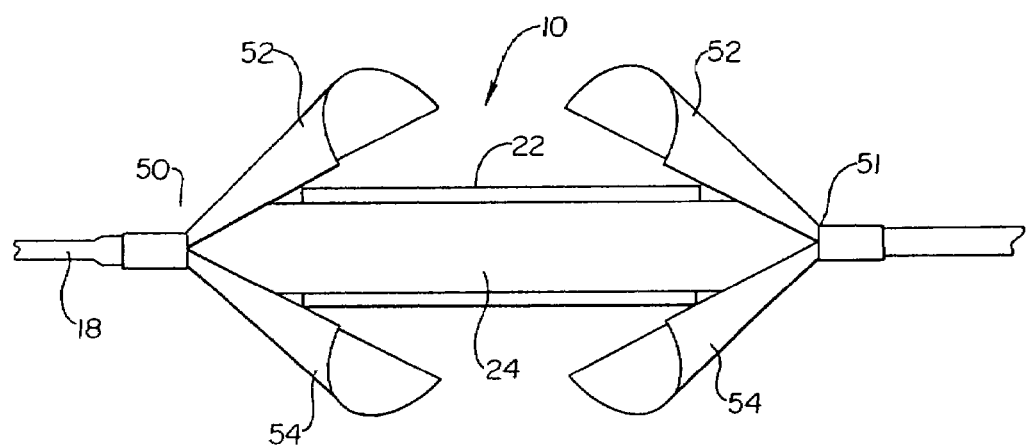
FIG. 13 is a side elevational view of an embodiment of the invention wherein a catheter having winged sleeves is shown with the sleeves in the released state.

The released position shown in FIG. 13 represents a radially oriented lifting of the winged members 52 and 54 away from the shaft 18. However, the winged members 52 and 54 may also be configured to be removed from the medical device receiving region 22 by way of longitudinal retraction such as by foreshortening and/or rolling back of the winged portions 52 and 54. The winged portions 52 and 54 extend from a first portion 53 of the sleeve 50, which is constructed and arranged to be engaged to a portion of a catheter shaft 18.

When disposed about a catheter shaft 18 in the retaining position, the wing members 52 and 54 preferably have sufficient radial strength to retain a stent 24 on a catheter 10 and to prevent a self-expanding medical device from radially expanding. To prevent the stent 24 from prematurely expanding, the winged members 52 and 54 may be provided with securement members 56 such as may be seen in FIG. 11. Securement members 56 are preferably strands of material which are disposed about the sleeve(s) 50 and 51. Securement members 56 may be frangible and configured to rupture or break when the winged members 52 and 54 are transitioned from the retaining position to the released position. The securement members 56 may also be biodegradable such that when the catheter 10 is advanced to a desired position, body fluids will react with the securement members 56 causing them to erode or otherwise degrade, thereby releasing the winged members 52 and 54 for transition.

Figure 11:
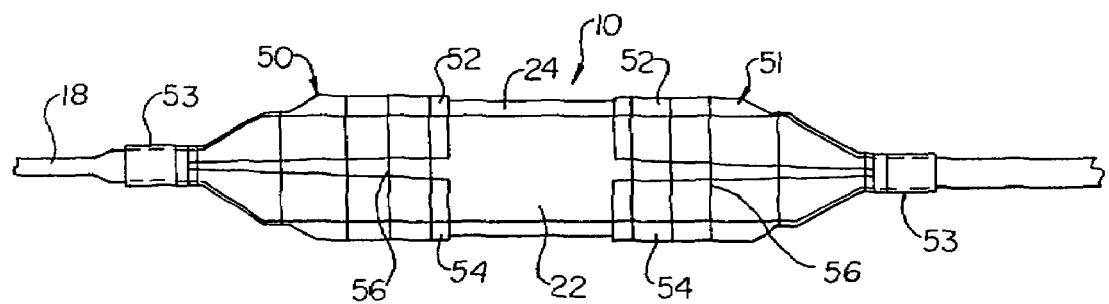
FIG. 11 is a side elevational view of an embodiment of the invention similar to that shown in FIG. 10, wherein the winged sleeves further comprise tying members.

In a preferred embodiment securement members 56 are constructed from a SMM and are provided with a default or retaining radius such as may be seen in FIG. 11. When the winged members 52 and 54 are exposed to a transition condition to cause the winged members 52 and 54 to transition from the retaining position to the released position, the securement members 56 may radially expand to a programmed radius which is sufficient to allow the winged members 52 and 54 to release the stent 24.

In an alternative embodiment of the invention, the wing members 52 and/or 54 are at least partially constructed from a non-SMP material along with the securement members 56. For example, in the case of a balloon expandable stent such as may be seen in FIGS. 16-20, the sleeves 50 could be a standard polymer material, or even a balloon material such as DynaLEAP. As the balloon expands, the securement members 56 will break from the pressure and the wing members 52 and 54 are released.

Figure 12:
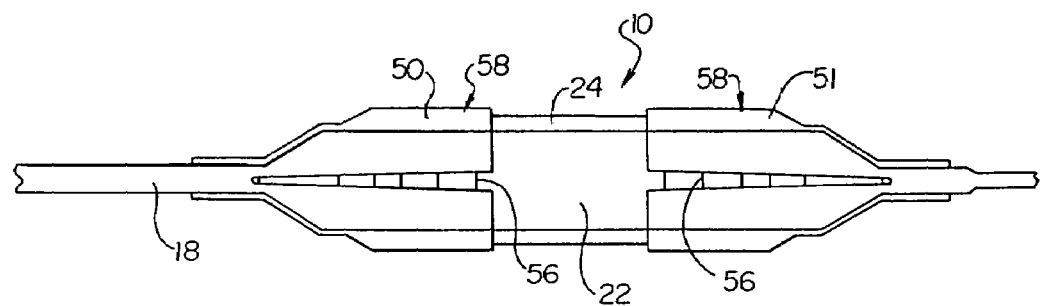
FIG. 12 is a side elevational view of an embodiment of the invention similar to that shown in FIG. 1 wherein the winged sleeve further comprise covering sleeves.

In yet another embodiment shown in FIG. 12, a covering sleeve 58 may be placed over the sleeves 50 and 51, and securement members 56, to provide the catheter with a smoother profile for improved trackability within a body lumen.

In at least one embodiment, the covering sleeve 58 may be a thin membrane of biodegradable material and/or a coating of lubricant. Alternatively, the covering sleeve 58 is constructed of the same material as sleeve(s) 50 and may be withdrawn from the medical device receiving region 22 in the same manner.

Figure 14:
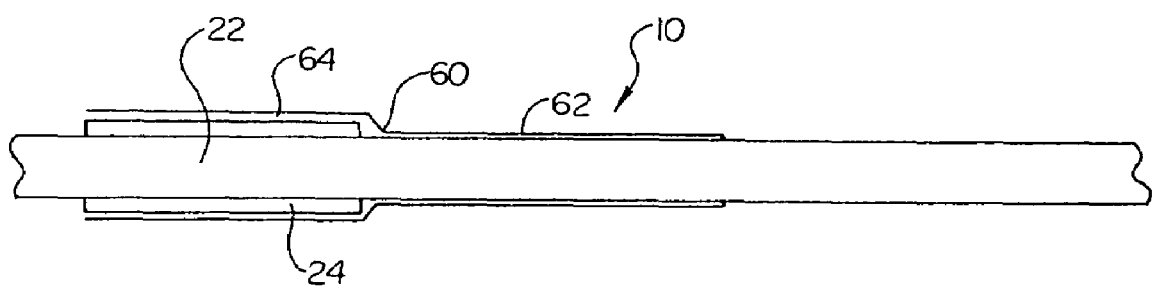
FIG. 14 is a side elevational view of an embodiment of the invention wherein a catheter is shown equipped with a retractable body sheath.
Figure 15:
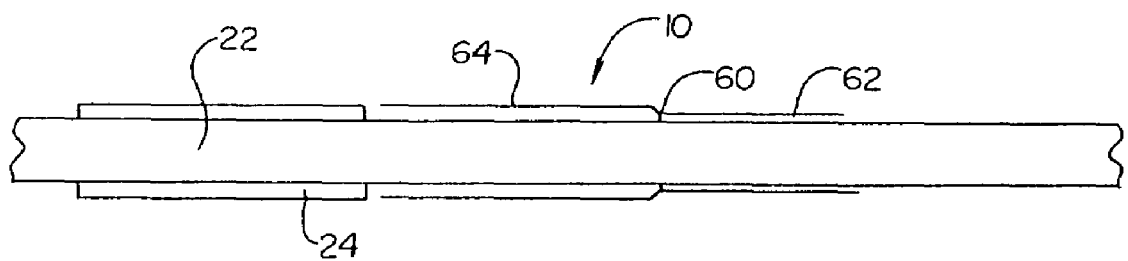
FIG. 15 is a side elevational view of the embodiment shown in FIG. 14 wherein the body sheath is shown in a retracted state.

In yet another embodiment of the invention shown in FIGS. 14 and 15, a single sleeve or sheath 60, may employ SMM in a first portion 62 to draw a second portion 64 from the medical device receiving region 22 and any stent 24 positioned thereabout. At least a portion of the first portion 62 may be engaged to the catheter shaft 18 in any manner, such as have been previously described. When in the programmed state, shown in FIG. 14, the length of the first portion 62 is sufficient to allow the second portion 64 to be drawn over at least a portion of the medical device receiving region 22. When a transition condition is present the first portion 62 will contract to its default state shown in FIG. 15, thereby withdrawing the second portion 64 from the medical device receiving region 22 and any associated stent 24. In an alternative embodiment the first portion 62 may be comprised of one or more strands of elastic and/or SMP material. Preferably, the first portion 62 is at least partially constructed from a lubricious material, or includes a lubricious coating on its interior and/or exterior surface. In a most preferred embodiment the first portion is configured to retract off of a stent 24 without damaging or otherwise impairing the structure or performance of a drug coating present on the stent 24.

In addition to providing a catheter 10 with a retractable sleeve 60, in the embodiment shown in FIGS. 16 and 17, a catheter may also be equipped with a distally mounted sleeve 50 having winged members 52 and 54. As is shown in FIG. 16, the winged sleeve 50 may overlap the distal end 66 of the retractable sleeve 60 prior to the introduction of a transition condition. The winged sleeve 50 may be configured to secure the retractable sleeve 60 thereby preventing unintended or premature retraction of sleeve 60. When the transition condition is present, the winged portions 52 and 54 are placed in the released state, thereby releasing the sleeve 60 to retract from the stent 24, such as is shown in FIG. 17. In those embodiments where the winged sleeve 50 actively prevents the sleeve 60 from retracting, the second portion 64 of sleeve 60 may be constructed from materials other than SMM materials.

In FIG. 18 an alternative embodiments of the invention is shown wherein the catheter 10 equipped with winged sleeve 50 and retracting sleeve 60 as described above, but also a protective sheath 70 which ensures that the second portion 64 of the retracting sleeve 60 remains immediately adjacent to the catheter shaft 18 during retraction. As is illustrated in FIG. 18, the sheath 70 also acts as a guide to ensure uniform retraction and receipt of the first portion 62.

In another embodiment shown in FIG. 18 a protective sheath 70 is present which serves to both cover and protect the stretch elastic strands of the first portion 62. The sheath 70 also acts as a housing or stop for sheath or sleeve 60 when it is retracted. The protective sheath 70 may allow some or all, of the second portion 64 to be pulled into the sheath 70 when the sleeve 60 is retracted. The protective sheath 70 may be configured to halt or limit retraction of the sleeve 60.

In yet another embodiment, shown in FIGS. 19 and 20, the catheter 10 such as was described in regard to FIG. 18 above, further comprises a proximally mounted winged sleeve 51 wherein winged portions 52 and 54 are disposed about a portion of the stent 24 and the first portion 53 is engaged to the sheath 70. When a transition condition occurs the winged sleeves 50 and 51 are placed in the released state, and the retracting sleeve 60 is retracted into the sheath 70 such as is shown in FIG. 20.

In some embodiments, the second portion 64 of sleeve 60 may be characterized as being comprised of one or more strands or filaments 65 of sleeve material. The distal end of the sleeve is retained under the winged sleeve 50 such as previously described, but one or more securement members 56, such as are shown in FIG. 16 are disposed about the winged sleeve 50 to secure the wings 52 and 54 about the stent 24 prior to delivery. Prior to stent delivery, the second portion 64 of sleeve 60 may also have one or more securement members disposed thereabout.

In some embodiments of the invention, such as are shown for example in FIGS. 14-20, a catheter 10 utilizes a preloaded elastic force retraction process such as is shown. In the various embodiments shown the first portion 62 may comprise multiple elastic strands that are attached proximal to the receiving region 22 of the catheter shaft 18. At least one of the elastic strands are stretched proximally from the receiving region 22 to create a preloaded retraction force that will act on the second portion 64 of the sheath or sleeve 60 when the retraction trigger is activated.

As is shown in FIG. 16 the sheath is stretched distally causing a force to be stored in the stretched elastic bands of the first portion 62. When the second portion 64 is fully in place covering the device as needed the wing 50 is placed over the distal end of the second portion of sheath 64 and tied in place with ties 56.

When the retraction trigger is activated, such as by initiation of balloon inflation, ties 56 will break thereby initiating sleeve retraction. As a result, the preloaded force stored within the stretched first portion 62 causes the sleeve 60 to begin withdrawing proximally to uncover the receiving region 22. The direction of travel of retraction is indicated by the arrow shown in FIG. 17.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A retractable sleeve for use with a catheter, the sleeve comprising:
a tubular member constructed and arranged to transition between an extended state and a retracted state, the tubular member further having a first portion and a second portion, the second portion being at least partially constructed from a shape memory material and the first portion is constructed and arranged to be engaged to at least a portion of a catheter shaft and in the extended state the second portion constructed and arranged to at least partially overlay a medical device receiving region of the catheter shaft, and the second portion further constructed and arranged to respond to a transition stimulation in order to transition from the extended state to the retracted state, the transition stimulation selected from at least one member of the group consisting of ultrasonic energy, electrical stimulations, chemical stimulations, heat stimulations, optical stimulations, and any combination thereof.

2. The sleeve of claim 1 wherein at least one of the first portion and the second portion of the tubular member are at least partially constructed from a non-shape memory material.

3. The sleeve of claim 1 wherein at least one portion of the tubular member is comprised of at least one strand of sleeve material.

4. The sleeve of claim 3 wherein at least one of the strands is made from a shape memory material.

5. The sleeve of claim 3 wherein at least one of the strands is made from a non-shape memory material.

6. The sleeve of claim 1 wherein in the retracted state the second portion is constructed and arranged to be longitudinally retracted from the medical device receiving region.

7. The sleeve of claim 1 wherein in the retracted state the second portion is constructed and arranged to be rollingly retracted from the medical device receiving region.

8. The sleeve of claim 1 wherein in the retracted state the second portion is constructed and arranged to radially expand off of the medical device receiving region.

9. The sleeve of claim 1 wherein in the extended state, the second portion is constructed and arranged to extend over the entire medical device receiving region of the catheter.

10. The sleeve of claim 1 wherein the second portion comprises at least two winged members, the at least two winged members extending from the first portion, in the extended state the at least two winged members constructed and arranged to at least partially overlay the medical device receiving region of the catheter shaft, in the retracted state the at least two winged members being removed from the medical device receiving region.

11. The sleeve of claim 10 wherein the at least two winged members in the extended state are constructed and arranged to provide sufficient radial strength to retain a medical device in an unexpanded state about the medical device receiving region.

12. The sleeve of claim 10 further comprising at least one securement member, in the extended state the at least one securement member is disposed about the at least two winged members and being constructed and arranged to secure at least a portion of each of the at least two winged members over at least a portion of the medical device receiving region, in the retracted state the at least one securement member being removed from about the at least two winged members.

13. The sleeve of claim 12 further comprising a covering layer, the covering layer overlaying at least a portion of the at least one securement member and the at least two winged members.

14. The sleeve of claim 12 further comprising a covering layer, the covering layer overlaying at least a portion of the at least one securement member and the tubular member.

15. The sleeve of claim 1 wherein, the shape memory material is selected from at least one member of the group consisting of: shape memory metal; natural rubber; shape memory polymers and any combination thereof.

16. A catheter comprising:
a catheter shaft, at least a portion of the catheter shaft defining a medical device receiving region; and
a first sleeve, the first sleeve comprising a tubular member constructed and arranged to transition between an extended state and a retracted state, the tubular member having a first portion and a second portion, the first portion being engaged to the catheter shaft, the first portion exerting a preloaded elastic proximal force on the second portion, in the extended state the second portion extending over the medical device receiving region, in the retracted state the second portion does not extend over the medical device receiving region, the second portion retracting along a longitudinal axis from the extended state to the retracted state due to the preloaded elastic proximal force of the first portion.

17. The catheter of claim 16 further comprising a second sleeve, the second sleeve constructed and arranged to transition between an extended state and a retracted state, the second sleeve comprising a first portion and a second portion,
the second portion comprising winged members, at least a portion of the winged members overlapping an end region of the second portion of the first sleeve when the second sleeve is in the extended state and the first sleeve is in the extended state, the second portion of the second sleeve not overlapping the end region of the second portion of the first sleeve when the second sleeve is in the retracted state.

18. The catheter of claim 16, further comprising at least one securement member disposed about a circumference of the second portion of the first sleeve when the first sleeve is in the retracted state.

19. The catheter of claim 16 wherein the first portion of the first sleeve comprises a multiplicity of elastic strands.

20. A catheter comprising:
a catheter shaft, at least a portion of the catheter shaft defining a medical device receiving region;
a first sleeve, the first sleeve comprising a tubular member constructed and arranged to transition between an extended state and a retracted state, the tubular member having a first portion and a second portion, the first portion being engaged to the catheter shaft, the first portion at least partially constructed from a shape memory material, in the extended state the second portion extending over at least a portion of the medical device receiving region and the first portion has a first length, in the retracted state the second portion does not extend about the medical device receiving region and the first portion has a second length less than the first length.

* * * * *